(12) United States Patent
Takaya

(10) Patent No.: US 6,394,959 B1
(45) Date of Patent: May 28, 2002

(54) CONTINUOUS BLOOD-PRESSURE MONITOR APPARATUS

(75) Inventor: Masami Takaya, Aichi-ken (JP)

(73) Assignee: Colin Corporation, Komaki (JP)

( * ) Notice: Subject to any disclaimer, the term of this patent is extended or adjusted under 35 U.S.C. 154(b) by 28 days.

(21) Appl. No.: 09/610,307

(22) Filed: Jul. 5, 2000

(51) Int. Cl.$^7$ ............................................. A61B 5/00
(52) U.S. Cl. ..................................... 600/485; 600/500
(58) Field of Search .............................. 600/481, 485, 600/490, 493–496, 500

(56) References Cited

U.S. PATENT DOCUMENTS

| | | | | |
|---|---|---|---|---|
| 5,439,002 A | * | 8/1995 | Narimatsu et al. | 600/500 |
| 5,590,661 A | * | 1/1997 | Ohmori et al. | 600/500 |
| 5,762,610 A | * | 6/1998 | Narimatsu et al. | 600/502 X |
| 5,908,027 A | * | 6/1999 | Butterfield et al. | 600/485 X |

* cited by examiner

Primary Examiner—Robert L. Nasser
(74) Attorney, Agent, or Firm—Oliff & Berridge, PLC

(57) ABSTRACT

A blood-pressure monitor apparatus including a pulse-wave sensor including pressure sensing elements, a pressing device which presses the pulse-wave sensor against an artery via skin tissue, a selecting device for selecting, as an optimum element, one of the pressure sensing elements, a determining means for changing the pressing force of the pressing device and determining, based on the pulse wave detected by the optimum element while the pressing force is changed, an optimum pressing force with which the pressing device presses the pulse wave sensor against the artery such that a portion of a wall of the artery is flattened, a maintaining device for maintaining the optimum pressing force of the pressing device, a determining means for determining an estimated blood pressure according to a predetermined relationship between blood pressure and magnitude of pressure pulse wave, based on a magnitude of each of heartbeat-synchronous pulses of the pulse wave detected by the optimum element in a state in which the pulse-wave sensor is pressed against the artery with the maintained optimum pressing force, and a display device which displays, in a two-dimensional coordinate system, a curve representing a change of respective amplitudes of heartbeat-synchronous pulses of the pulse wave detected by the optimum element, with respect to a change of the pressing force of the pressing device.

10 Claims, 10 Drawing Sheets

CONTINUOUS BLOOD-PRESSURE MONITOR APPARATUS

BACKGROUND OF THE INVENTION

1. Field of the Invention

The present invention relates to a continuous blood-pressure monitor apparatus which continuously monitors blood pressure of a living subject based on a pressure pulse wave detected by a pressure-pulse-wave sensor, and particularly to the art of appropriately pressing the pressure-pulse-wave sensor against an artery of the subject via body surface of the subject.

2. Related Art Statement

U.S. Pat. No. 5,762,610 discloses a continuous blood-pressure ("BP") monitor apparatus which continuously monitors the BP of a living subject. This BP monitor apparatus includes (a) a pressure-pulse-wave ("PPW") sensor which includes a plurality of pressure sensing elements which are arranged in a reference direction and each of which detects a PPW propagated thereto from an arterial vessel of the subject and produces a PPW signal representing the detected PPW that includes a plurality of heartbeat-synchronous pulses, the PPW sensor having a press surface which supports the pressure sensing elements arranged in the reference direction and which is adapted to be pressed against the arterial vessel via a body surface or skin of the subject such that the arranged pressure sensing elements intersect the arterial vessel; (b) a pressing device which presses, with a pressing force, the PPW sensor against the arterial vessel via the body surface; (c) optimum-element selecting means for selecting, as an optimum element, one of the pressure sensing elements that provides the detected PPW including a heartbeat-synchronous pulse whose amplitude is greatest of respective amplitudes of respective heartbeat-synchronous pulses of the detected PPWs provided by the pressure sensing elements; (d) optimum-pressing-force determining means for changing the pressing force of the pressing device and determining, based on the PPW detected by the optimum element while the pressing force is changed, an optimum pressing force with which the pressing device presses the PPW sensor against the arterial vessel via the body surface such that a portion of a wall of the arterial vessel is substantially flattened; (e) optimum-pressing force maintaining means for maintaining the optimum pressing force of the pressing device; and (f) estimated-BP determining means for determining an estimated BP value according to a predetermined relationship between BP and magnitude of PPW, based on a magnitude of each of a plurality of heartbeat-synchronous pulses of the detected PPW represented by the PPW signal produced by the optimum element in a state in which the PPW sensor is pressed against the arterial vessel with the optimum pressing force maintained by the optimum-pressing-force maintaining means. The BP monitor apparatus monitors the BP of the subject by successively determining the estimated BP values of the subject.

The estimated BP values successively determined by the above BP monitor apparatus cannot accurately reflect actual BP values of the subject unless the PPW sensor is appropriately pressed against the arterial vessel via the body surface such that a portion of the wall of the artery is substantially flattened. However, the prior BP monitor apparatus does not display the optimum pressing force of the pressing device determined by the optimum-pressing-force determining means, or displays the optimum pressing force alone. Therefore, it is difficult for an operator who operates the prior BP monitor apparatus to judge, from what is displayed thereby, whether the optimum pressing force has been determined in an appropriate state in which a portion of the wall of the artery is stably flattened and accordingly the appropriate state can last for a long time, or in an inappropriate state in which a portion of the wall of the artery is considerably unstably flattened and accordingly the state in which the portion of the wall of the artery is flattened cannot last for so long a time.

SUMMARY OF THE INVENTION

It is therefore an object of the present invention to provide a blood-pressure monitor apparatus which assures that an operator can recognize how the apparatus presses an arterial vessel of a living subject at the time of determination of an optimum pressing force.

(1) According to a first feature of the present invention, there is provided a blood-pressure monitor apparatus for monitoring a blood pressure of a living subject, comprising a pressure-pulse-wave sensor which includes a plurality of pressure sensing elements which are arranged in a reference direction and each of which detects a pressure pulse wave propagated thereto from an arterial vessel of the subject and produces a pressure-pulse-wave signal representing the detected pressure pulse wave that includes a plurality of heartbeat-synchronous pulses, the pressure-pulse-wave sensor having a press surface which supports the pressure sensing elements arranged in the reference direction and which is adapted to be pressed against the arterial vessel via a body surface of the subject such that the arranged pressure sensing elements intersect the arterial vessel; a pressing device which presses, with a pressing force, the pressure-pulse-wave sensor against the arterial vessel via the body surface; optimum-element selecting means for selecting, as an optimum element, one of the pressure sensing elements that provides the detected pressure pulse wave including a heartbeat-synchronous pulse whose amplitude is greatest of respective amplitudes of respective heartbeat-synchronous pulses of the detected pressure pulse waves provided by the pressure sensing elements; optimum-pressing-force determining means for changing the pressing force of the pressing device and determining, based on the pressure pulse wave detected by the optimum element while the pressing force is changed, an optimum pressing force with which the pressing device presses the pressure-pulse wave sensor against the arterial vessel via the body surface such that a portion of a wall of the arterial vessel is substantially flattened; optimum-pressing-force maintaining means for maintaining the optimum pressing force of the pressing device; estimated-blood-pressure determining means for determining an estimated blood pressure according to a predetermined relationship between blood pressure and magnitude of pressure pulse wave, based on a magnitude of each of a plurality of heartbeat-synchronous pulses of the detected pressure pulse wave represented by the pressure-pulse-wave signal produced by the optimum element in a state in which the pressure-pulse-wave sensor is pressed against the arterial vessel with the optimum pressing force maintained by the optimum-pressing-force maintaining means; and an amplitude-change-curve displaying device which displays, in a two-dimensional coordinate system having a first axis indicative of pressing force and a second axis indicative of amplitude of heartbeat-synchronous pulse of pressure pulse wave, an amplitude-change curve representing a change of the respective amplitudes of the heartbeat-synchronous pulses of the pressure pulse wave detected by the optimum element, with respect to a change of the pressing force of the pressing device caused by the optimum-pressing-force determining means.

According to this feature, the amplitude-change-curve displaying device displays the amplitude-change curve representing the change of the respective amplitudes of the heartbeat-synchronous pulses of the pressure pulse wave detected by the optimum element, with respect to the change of the pressing force of the pressing device caused by the optimum-pressing-force determining means. Therefore, an operator who operates the present BP monitor apparatus can recognize how the apparatus presses the arterial vessel of the subject at the time of determination of the optimum pressing force.

(2) According to a second feature of the present invention that includes the first feature (1), the blood-pressure monitor apparatus further comprises an estimated blood-pressure displaying device which displays the estimated blood pressure determined by the estimated-blood-pressure determining means.

(3) According to a third feature of the present invention that includes the first or second feature (1) or (2), the blood-pressure monitor apparatus further comprises an optimum-pressing-force displaying device which displays, in the two-dimensional coordinate, system in which the amplitude-change curve is displayed, a symbol representing the optimum pressing force determined by the optimum-pressing-force determining means. According to this feature, the operator can judge whether the optimum pressing force has been determined at an appropriate pressing force.

(4) According to a fourth feature of the present invention that includes any one of the first to third features (1) to (3), the blood-pressure monitor apparatus further comprises judging means for judging, based on the pressure pulse wave detected by the optimum element while the pressing force is changed by the optimum-pressing-force determining means, whether the pressing device appropriately presses the pressure-pulse-wave sensor against the arterial vessel via the body surface. According to this feature, the judging means can identify an inappropriate state in which a space is left between the PPW sensor and the body surface because the arterial vessel is too shallow under the body surface and accordingly the optimum pressing force determined by the optimum-pressing-force determining means is too small, and an inappropriate state in which the PPW sensor cannot be pressed with a sufficiently great pressing force because the artery is too deep under the body surface and accordingly the optimum pressing force determined by the optimum-pressing-force determining means is too great to be applied by the pressing device. Thus, the present BP monitor apparatus can automatically judge whether the state in which the PPW sensor is pressed against the artery is appropriate.

(5) According to a fifth feature of the present invention that includes any one of the first to fourth features (1) to (4), the blood-pressure monitor apparatus further comprises a blood-pressure measuring device which includes an inflatable cuff adapted to be wound around a body portion of the subject and measures at least one blood pressure value of the subject based on a pulse wave transmitted to the cuff while an air pressure in the cuff is changed; and a relationship determining means for determining the relationship between blood pressure and magnitude of pressure pulse wave, based on the at least one blood pressure value measured by the blood-pressure measuring device and at least one magnitude of a heartbeat-synchronous pulse of the pressure pulse wave detected by the optimum element in the state in which the pressure-pulse-wave sensor is pressed against the arterial vessel with the optimum pressing force maintained by the optimum-pressing-force maintaining means.

(6) According to a sixth feature of the present invention, there is provided a blood-pressure monitor apparatus for monitoring a blood pressure of a living subject, comprising a pressure-pulse-wave sensor which includes a plurality of pressure sensing elements which are arranged in a reference direction and each of which detects a pressure pulse wave propagated thereto from an arterial vessel of the subject and produces a pressure-pulse-wave signal representing the detected pressure pulse wave that includes a plurality of heartbeat-synchronous pulses, the pressure-pulse-wave sensor having a press surface which supports the pressure sensing elements arranged in the reference direction and which is adapted to be pressed against the arterial vessel via a body surface of the subject such that the arranged pressure sensing elements intersect the arterial vessel; a pressing device which presses, with a pressing force, the pressure-pulse-wave sensor against the arterial vessel via the body surface; optimum-element selecting means for selecting, as an optimum element, one of the pressure sensing elements that provides the detected pressure pulse wave including a heartbeat-synchronous pulse whose amplitude is greatest of respective amplitudes of respective heartbeat-synchronous pulses of the detected pressure pulse waves provided by the pressure sensing elements; optimum-pressing-force determining means for changing the pressing force of the pressing device and determining, based on the pressure pulse wave detected by the optimum element while the pressing force is changed, an optimum pressing force with which the pressing device presses the pressure-pulse wave sensor against the arterial vessel via the body surface such that a portion of a wall of the arterial vessel is substantially flattened; optimum-pressing-force maintaining means for maintaining the optimum pressing force of the pressing device; estimated-blood-pressure determining means for determining an estimated blood pressure according to a predetermined relationship between blood pressure and magnitude of pressure pulse wave, based on a magnitude of each of a plurality of heartbeat-synchronous pulses of the detected pressure pulse wave represented by the pressure- pulse-wave signal produced by the optimum element in a state in which the pressure-pulse-wave sensor is pressed against the arterial vessel with the optimum pressing force maintained by the optimum-pressing-force maintaining means; and a signal-magnitude-change-curve displaying device which displays, in a two-dimensional coordinate system having a first axis indicative of pressing force and a second axis indicative of magnitude of pressure-pulse-wave signal, a signal-magnitude-change curve representing a change of respective magnitudes of respective predetermined periodic points of the heartbeat-synchronous pulses of the detected pressure pulse wave represented by the pressure-pulse-wave signal produced by the optimum element, with respect to a change of the pressing force of the pressing device caused by the optimum-pressing-force determining means.

According to this feature, the signal-magnitude-change-curve displaying device displays the signal-magnitude-change curve representing the change of respective magnitudes of respective predetermined periodic points of the heartbeat-synchronous pulses of the detected PPW represented by the PPW signal produced by the optimum element, with respect to the change of the pressing force of the pressing device caused by the optimum-pressing-force determining means. Therefore, an operator who operates the present BP monitor apparatus can recognize how the apparatus presses the arterial vessel of the subject at the time of determination of the optimum pressing force.

(7) According to a seventh feature of the present invention that includes the sixth feature (6), the blood-pressure monitor apparatus further comprises an estimated-blood-pressure displaying device which displays the estimated blood pressure determined by the estimated-blood-pressure determining means.

(8) According to an eighth feature of the present invention that includes any one of the sixth or seventh feature (6) or (7), the blood-pressure monitor apparatus further comprises an optimum-pressing-force displaying device which displays, in the two-dimensional coordinate system in which the signal-magnitude-change curve is displayed, a symbol representing the optimum pressing force determined by the optimum-pressing-force determining means. According to this feature, the operator can judge whether the optimum pressing force has been determined at an appropriate pressing force.

(9) According to a ninth feature of the present invention that includes any one of the sixth to eighth features (6) to (8), the blood-pressure monitor apparatus further comprises judging means for judging, based on the pressure pulse wave detected by the optimum element while the pressing force is changed by the optimum-pressing-force determining means, whether the pressing device appropriately presses the pressure-pulse-wave sensor against the arterial vessel via the body surface.

(10) According to a ninth feature of the present invention that includes any one of the sixth to ninth features (6) to (9), the blood-pressure monitor apparatus further comprises a blood-pressure measuring device which includes an inflatable cuff adapted to be wound around a body portion of the subject and measures at least one blood pressure value of the subject based on a pulse wave transmitted to the cuff while an air pressure in the cuff is changed; and a relationship determining means for determining the relationship between blood pressure and magnitude of pressure pulse wave, based on the at least one blood pressure value measured by the blood-pressure measuring device and at least one magnitude of a heartbeat-synchronous pulse of the pressure pulse wave detected by the optimum element in the state in which the pressure-pulse-wave sensor is pressed against the arterial vessel with the optimum pressing force maintained by the optimum-pressing-force maintaining means.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Hereinafter, there will be described a continuous blood-pressure ("BP") monitor apparatus embodying the present invention, by reference to the drawings. The present BP monitor apparatus is used for monitoring the BP condition of a patient during, or after, a surgical operation, or a living subject during an exercise test.

Figure 1:
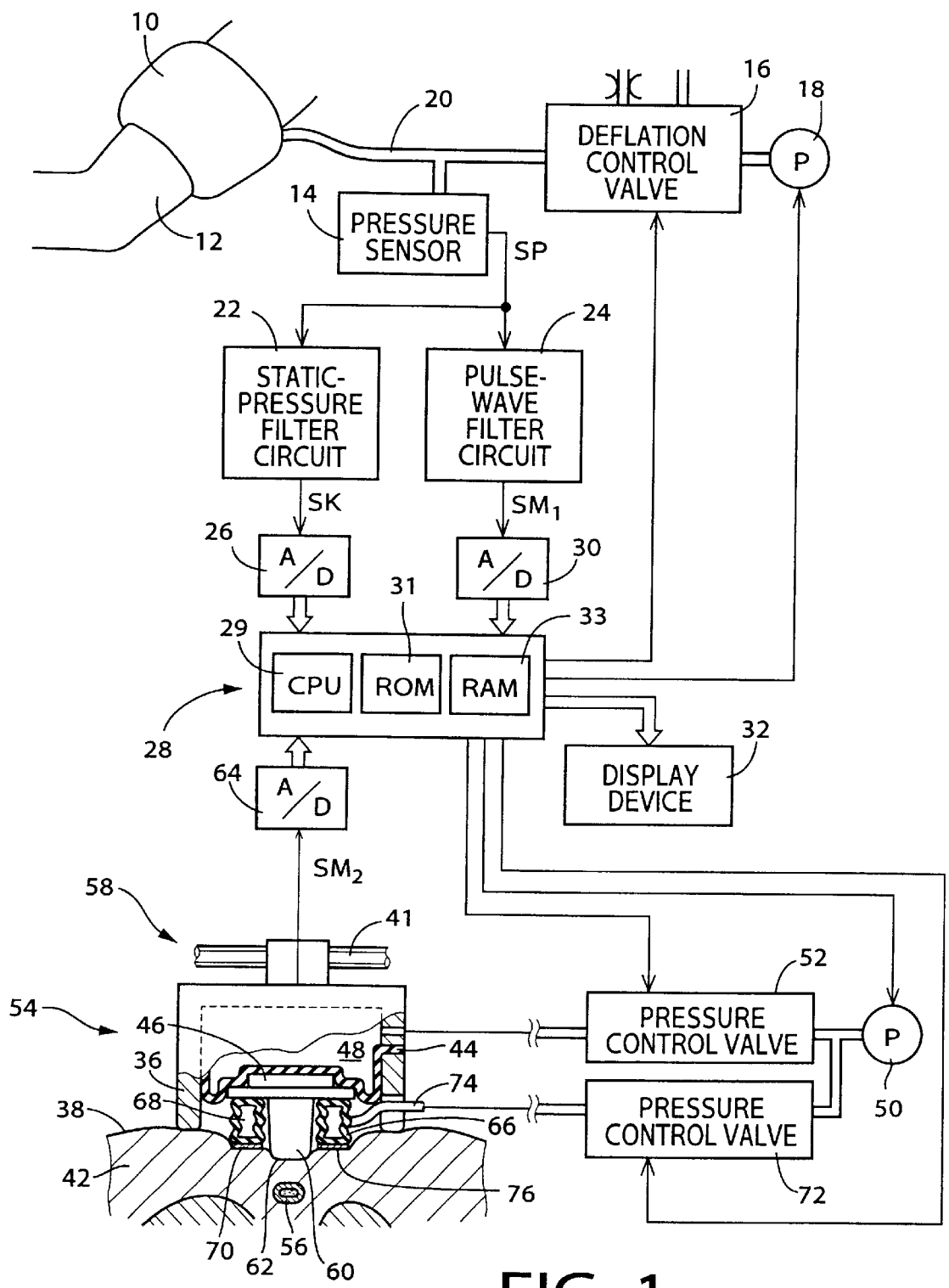
FIG. 1 is a diagrammatic view for explaining the construction of a continuous blood-pressure ("BP") monitor apparatus to which the present invention is applied.

In FIG. 1, reference numeral 10 designates an inflatable cuff which includes a belt-like cloth bag and a rubber bag accommodated in the cloth bag and which is worn on a patient such that the cuff 10 is wound around an upper arm 12 of the patient. The cuff 10 is connected to a pressure sensor 14, a deflation control valve 16, and an air pump 18 via piping 20. The deflation control valve 16 is switchable to each of three operation states, i.e., a pressure-supply state in which the control valve 16 allows a pressurized air to be supplied from the air pump 18 to the cuff 10, a slow-deflation state in which the control valve 16 allows the pressurized air to be slowly deflated from the cuff 10, and a quick-deflation state in which the control valve 16 allows the pressurized air to be quickly deflated from the cuff 10.

The pressure sensor 14 detects an air pressure in the cuff 10, produces a pressure signal, SP, representing the detected air pressure, and supplies the pressure signal SP to a static-pressure filter circuit 22 and a pulse-wave filter circuit 24. The static-pressure filter circuit 22 includes a low-pass filter which extracts, from the pressure signal SP, a constant component representing a static pressure of the cuff, produces a cuff-pressure signal, SK, representing the static pressure, i.e., the cuff pressure, and supplies the cuff-pressure signal SK to a control device 28 via an analog-to-digital ("A/D") converter 26. The pulse-wave filter circuit 24 includes a band-pass filter which extracts, from the pressure signal SP, an oscillatory component representing a pulse wave transmitted to the cuff, produces a pulse-wave signal, $SM_1$, representing the cuff pulse wave, and supplies the pulse-wave signal $SM_1$ to the control device 28 via an A/D converter 30. The cuff pulse wave represented by the pulse-wave signal $SM_1$ is a pulse wave which is produced from a brachial artery (not shown) of the patient in synchronism with the heartbeat of the patient and is propagated from the brachial artery to the inflatable cuff 10. Thus, the pulse-wave filter circuit 24 provides a cuff-pulse-wave detecting device. The cuff pulse wave represented by the pulse-wave signal $SM_1$ consists of successive heartbeat-synchronous pulses which are successively produced from the brachial artery in synchronism with successive beats of the heart of the patient.

The control device 28 is constituted by a so-called microcomputer including a central processing unit ("CPU") 29, a read only memory ("ROM") 31, a random access memory ("RAM") 33, and an input-and-output ("I/O") port (not shown). The CPU 29 processes signals according to control programs pre-stored in the ROM 31, by utilizing a temporary-storage function of the RAM 33, and outputs, via the I/O port, drive signals to respective drive circuits (not shown) of the deflation control valve 16 and the air pump 18. Thus, the control device controls the control valve 16 and the air pump 18. When the present BP monitor apparatus carries out a BP measuring operation using the cuff 10, the control device 28 first increases the air pressure of the cuff 10 up to a predetermined target value (e.g., 180 mmHg) which is estimated to be sufficiently higher than a systolic BP value of the patient, and then decreases the Cuff pressure from the target value at a predetermined low rate, e.g., 3 mmHg/sec. Based on the change of respective amplitudes of successive heartbeat-synchronous pulses of the pulse-wave signal $SM_1$ obtained during the slow deflation of the cuff pressure, the control device 28 determines a systolic and a diastolic BP value (i.e., standard BP values) of the patient according to known oscillometric method or Korotkoff-sound method, and commands the display 32 to display the thus determined BP values.

The present BP monitor apparatus further includes a pressure-pulse-wave detecting probe 34 which includes a container-like sensor housing 36; a drive device 39 which includes an electric motor (not shown); a feed screw 41 which is threadedly engaged with the sensor housing 36 and is driven or rotated by the electric motor to move the sensor housing 36 in a widthwise direction of a radial artery 56 of a wrist of the patient; and a casing 37 which accommodates the sensor housing 36, the drive device 39, and the feed screw 41. A band 40 which is connected to the casing 37 is wound around a wrist 42 of one arm (e.g., left arm) of the patient that is opposite to the other arm (e.g., right arm) around which the cuff 10 is wound, in the state in which an open end of the sensor housing 36 is opposed to a body surface 38 of the patient.

As shown in FIG. 1, the sensor housing 36 accommodates a pressure-pulse-wave ("PPW") sensor 46, and supports the PPW sensor 46 via a rubber diaphragm 44 such that the PPW sensor 46 is movable relative to the sensor housing 36 and is projectable out of the open end of the housing 36. The housing 36 and the diaphragm 44 cooperate with each other to define a first pressure chamber 48 to which a pressurized air is supplied from an air pump 50 via a pressure control valve 52. Thus, the PPW sensor 46 is pressed on the body surface 38 with a pressing force corresponding to the air pressure in the first pressure chamber 48. In the present embodiment, the pressing force applied to the PPW sensor 46 is expressed in terms of the air pressure (mmHg) of the first pressure chamber 48.

The sensor housing 36 and the diaphragm 44 cooperate with each other to provide a pressing device 54 which presses the PPW sensor 46 against the radial artery 56 via the body surface 38; and the feed screw 41 and the electric motor (not shown) cooperate with each other to provide a pressing-position changing device, i.e., a widthwise-direction moving device 58 which moves the PPW sensor 46 in the widthwise direction of the radial artery 56 and thereby changes the position where the sensor 46 is pressed against the artery 56.

The PPW sensor 46 includes a protruding portion 60 which protrudes away from the diaphragm 44 toward the open end of the sensor housing 36. The protruding portion 60 has an end surface which provides a press surface 62 in which a number of semiconductor pressure-sensing elements (not shown) are provided in an array, at a predetermined interval of distance equal to about 0.2 mm, in the widthwise direction of the radial artery 56, i.e., a direction parallel to the feed screw 41 along which which the PPW sensor 46 is moved. When the press surface 62 is pressed against the radial artery 56 via the body surface 38 of the wrist 42, each of the pressure-sensing elements detects an oscillatory pressure wave which is produced from the radial artery 56 and is propagated to the press surface 62, that is, a pressure pulse wave ("PPW"), produces a PPW signal, $SM_2$, representing the detected PPW, and supplies the PPW signal $SM_2$ to the control device 28 via an A/D converter 64.

The PPW sensor 46 includes an annular portion which surrounds the central protruding portion 60, faces the body surface 38, and supports an annular rubber bellows 66 fixed thereto. The rubber bellows 66 is expansible and contractable in a direction in which the PPW sensor 46 is moved toward and away from the body surface 38. The rubber bellows 66 defines a second pressure chamber 68 therein. An annular plate 70 is fixed to one end of the bellows 66 that is opposite to the other end thereof fixed to the annular portion of the PPW sensor 46. The second pressure chamber 68 is supplied with a pressurized air from the air pump 50 via a pressure control valve 72 and a rubber pipe 74. Thus, when the first pressure chamber 48 is supplied with the pressurized air and the protruding portion 60 of the sensor 46 is pressed on the body surface 38, a press surface 76 of the annular plate 70 is pressed, together with the press surface 62 of the protrusion 60, on the body surface 38 of the wrist 42. An amount of projection of the press surface 62 of the protrusion 60 from the press surface 76 of the annular plate 70 can be adjusted by adjusting the air pressure of the second pressure chamber 68. Restrictor rings (not shown) are provided on the inner and outer wall surfaces of the rubber bellows 66, to prevent the bellows 66 from being irregularly deformed in radial directions thereof.

The CPU 29 of the control device 28 processes signals according to the control programs pre-stored in the ROM 31 by using the temporary-storage function of the RAM 33, and outputs, via the I/O port, drive signals to respective drive circuits (not shown) of the air pump 50 and the two pressure control valves 52, 72. Thus, the control device 28 controls the respective air pressures of the first and second pressure chambers 48, 68. When the present BP monitor apparatus is operated in a BP monitoring operation, the control device 28 determines, based on the PPW represented by the PPW signal $SM_2$ supplied from the PPW sensor 46 while the pressure of the first chamber 48 is slowly changed, the most appropriate or optimum pressing force, $P_{HDPO}$, that is applied to the PPW sensor 46 to substantially flatten a portion of the wall of the radial artery 56, and commands the pressure control valve 52 to maintain the thus determined optimum pressing force $P_{HDPO}$.

In addition, the control device 28 determines a maximum magnitude, $P_{Mmax}$, and a minimum magnitude, $P_{Mmin}$, of a heartbeat-synchronous pulse of the PPW signal $SM_2$ which is detected, in the state in which the pressure of the first chamber 48 is maintained at the optimum pressing force $P_{HDPO}$, by one pressure-sensing element (hereinafter, referred to as the "active element") of the array of pressure-sensing elements of the PPW sensor 46 that is positioned right above the radial artery 56 and produces the PPW signal $SM_2$ representing the PPW including a heartbeat-synchronous pulse whose amplitude is the greatest of the respective amplitudes of the respective heartbeat-synchronous pulses of the PPWs represented by the PPW signals $SM_2$ produced by the pressure-sensing elements of the PPW sensor 46. Based on the systolic BP value, $BP_{SYS}$, and the diastolic BP value, $BP_{DIA}$, measured using the cuff 10, and the determined maximum and minimum magnitudes $P_{Mmax}$, $P_{Mmin}$ of the PPW signal $SM_2$, the control device 28 determines a BP-PPW relationship between blood pressure BP and PPW magnitude $P_M$. According to the thus determined BP-PPW relationship, the control device 28 successively determines (i.e., estimates) a systolic and a diastolic monitor (i.e., estimated) BP value, $MBP_{SYS}$, $MBP_{DIA}$, of the patient based on a maximum and a minimum magnitude $P_{Mmax}$, $P_{Mmin}$ of each of successive heartbeat-synchronous pulses of the PPW signal $SM_2$ detected by the active element of the PPW sensor 46. The control device 28 commands the display 32 to successively display, in digits, the systolic and diastolic monitor BP values $MBP_{SYS}$, $MBP_{DIA}$ determined for the each pulse of the PPW signal $SM_2$, and continuously display a waveform representing the monitor BP values MBP continuously obtained by calibrating the PPW signal $SM_2$ according to the BP-PPW relationship.

Figure 3:
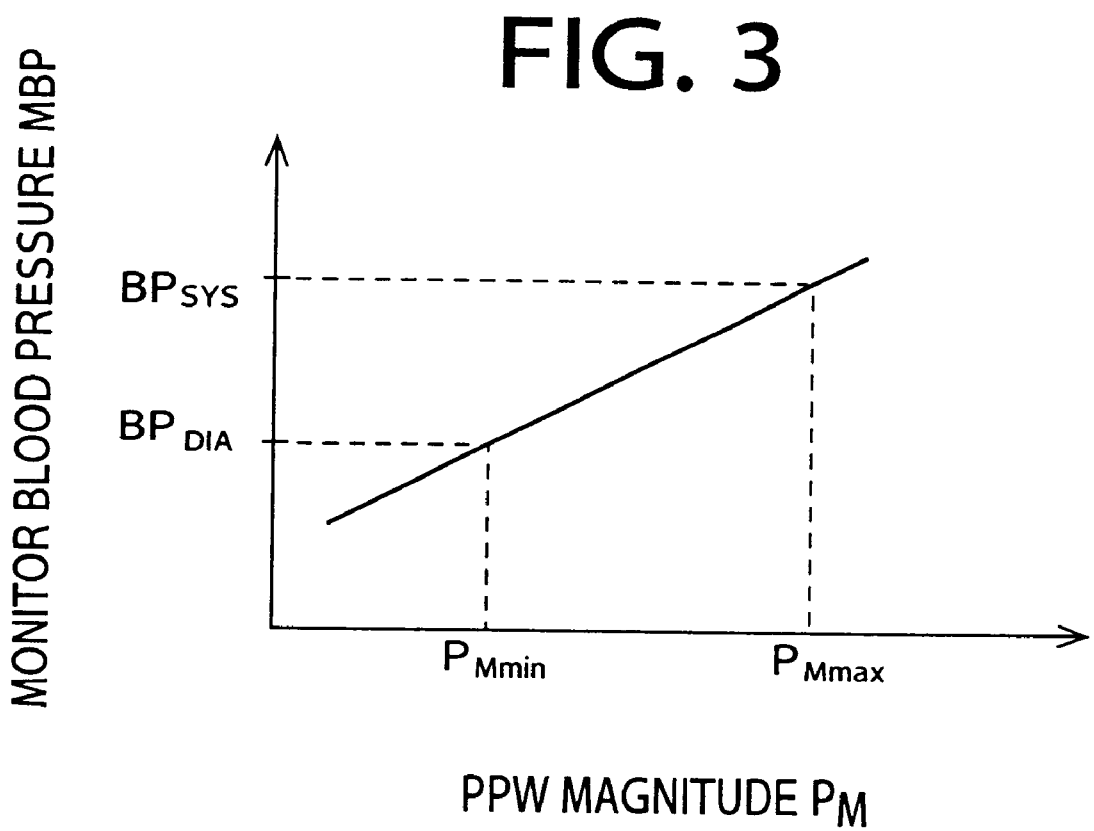
FIG. 3 is a graph showing a relationship between monitor blood pressure MBP and PPW magnitude $P_M$ that is determined by the apparatus of FIG. 1.

FIG. 3 shows an example of the BP-PPW relationship that is expressed by the following equation:

$$MBP = A \cdot P_M + B$$

where

A is a constant indicating a slope, and

B is a constant indicating an intercept.

Figure 4:
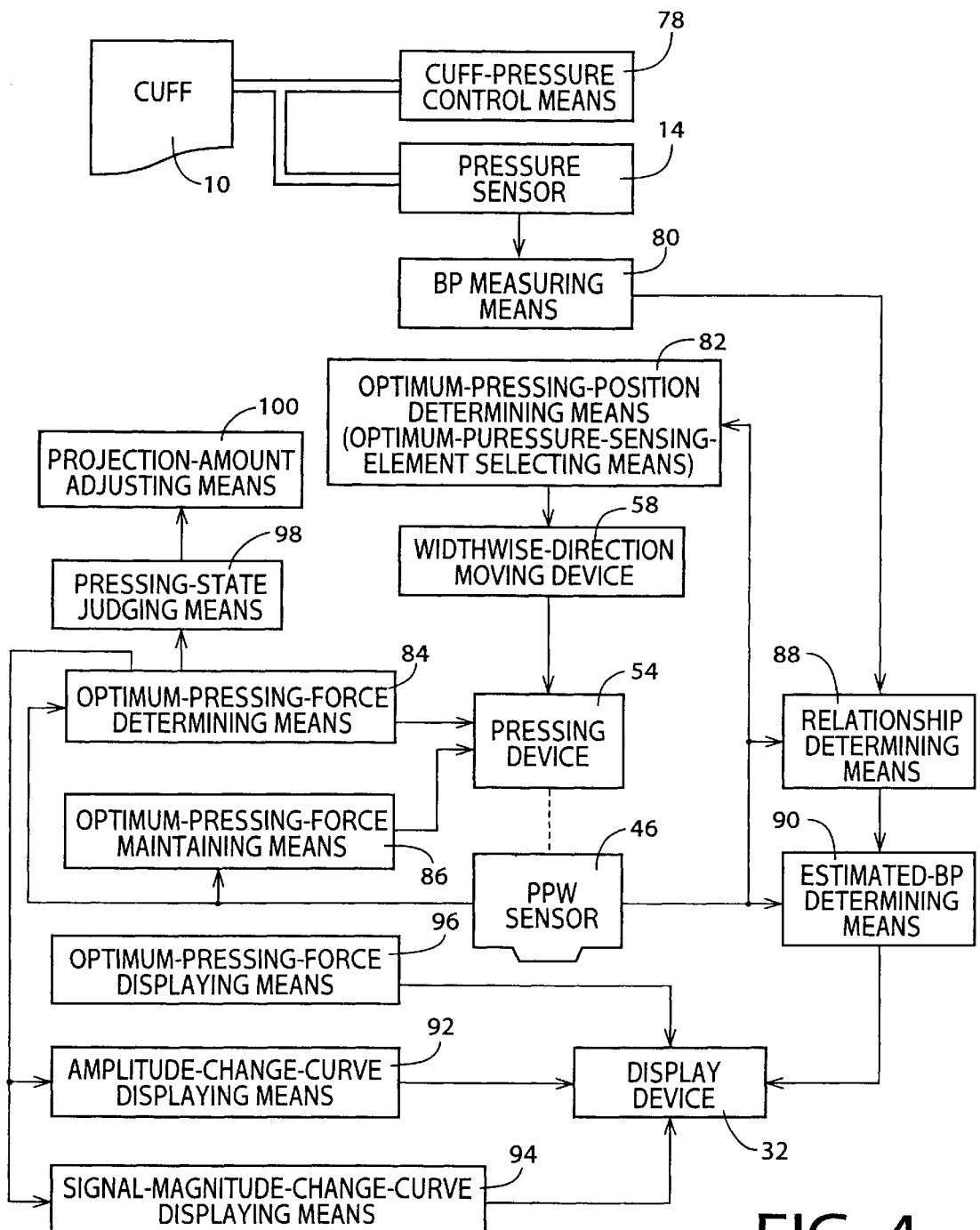
FIG. 4 is a diagrammatic view for explaining essential control functions of a control device of the apparatus of FIG. 1.

FIG. 4 shows essential control functions of the control device 28 of the continuous BP monitor apparatus constructed as described above. When a BP measurement is carried out, the pressure sensor 14 detects the pressing pressure of the cuff 10 that is changed by a cuff-pressure control means 78. A BP measuring means 80 measures a systolic BP value $BP_{SYS}$, a mean BP value $BP_{MEAN}$, and a diastolic BP value $BP_{DIA}$ (i.e., standard BP values), according to oscillometric method or Korotkoff-sound method. In the oscillometric method, the BP measuring means 80 determines the standard BP values based on the change of respective amplitudes of successive heartbeat-synchronous pulses of the pulse-wave signal $SM_1$ obtained by the pressure sensor 14 (or the pulse-wave filter circuit 24) while the pressing pressure of the cuff 10 is slowly changed at a predetermined rate of from 2 to 3 mmHg/sec. In the Korotkoff-sound method, the BP measuring means 80 determines the standard BP values based on the first and last detections of Korotkoff sounds by a microphone (not shown) while the cuff pressure is slowly changed at the predetermined rate.

An optimum-pressing-position determining means 82 determines an optimum pressing position where the PPW sensor 46 is most appropriately pressed against the radial artery 56 by the pressing device 54, when a predetermined pressing-position-determining condition is satisfied. The predetermined pressing-position-determining condition is, for example, when the PPW detecting probe 34 is initially worn on the patient, or when the above-explained active element of the PPW sensor 46 is identified as one of a predetermined number of elements present in each of opposite end portions of the array of pressure-sensing elements provided in the press surface 62. More specifically described, the optimum-pressing-position determining means 82 controls the pressing device 54 to press the PPW sensor 46 against the radial artery 56 with a first predetermined pressing force, $P_1$, which is sufficiently smaller than an optimum pressing force $P_{HDPO}$, described later, and judges whether the active element of the PPW sensor 46 is one of a predetermined number of elements present in a central portion of the array of pressure-sensing elements provided in the press surface 62. If a negative judgement is made, that is, if the active element of the PPW sensor 46 is not present in the central portion of the array of pressure-sensing elements, the means 82 controls the pressing device 54 to move once the PPW sensor 46 away from the body surface 38, subsequently controls the widthwise-direction moving device 58 to move the pressing device 54 and the PPW sensor 46 by a predetermined distance, and then controls the pressing device 54 again as described above and judges again as described above. On the other hand, if a positive judgment is made, that is, if the active element of the PPW sensor 46 is present in the central portion of the array of pressure-sensing elements, the means 82 judges that the PPW sensor 46 is positioned at the optimum pressing position, selects the active element of the PPW sensor 46 as an optimum pressure-sensing element of the same 46, and stores, in the RAM 33, data indicative of a sequential number which is given to the optimum element and represents the position of the optimum element in the array of pressure-sensing elements. Thus, the optimum-pressing-position determining means 82 also functions as an optimum-pressure-sensing-element selecting means.

An optimum-pressing-force determining means 84 controls the pressing device 54 positioned at the optimum pressing position by the means 82, to continuously increase the pressing force P applied thereby to the PPW sensor 46, and determines an optimum pressing force $P_{HDPO}$ based on the PPW represented by the PPW signal $SM_2$ which is produced by the optimum pressure-sensing element of the PPW sensor 46 while the pressing force P is increased. An initial pressing force, i.e., a minimum pressing force from which the pressing force P of the pressing device 54 is increased by the means 84, is experimentally determined, in advance, as a value which is sufficiently lower than the optimum pressing force $P_{HDPO}$ to be determined, even if different optimum pressing forces $P_{HDPO}$ may be determined for different individual patients. A terminal pressing force, i.e., a maximum pressing force at which the increasing of the pressing force P is ended, may be experimentally determined, in advance, as a value which is sufficiently higher than the optimum pressing force $P_{HDPO}$ to be determined, like the initial pressing force. Alternatively, the increasing of the pressing force P may be ended at a time when an amplitude-change curve, $C_A$, and/or a signal-magnitude-change curve, $C_S$, described later, are/is obtained during the increasing of the pressing force P and the optimum pressing force $P_{HDPO}$ is determined based on the amplitude-change curve $C_A$ and/or the signal-magnitude-change curve $C_S$.

Figure 5:
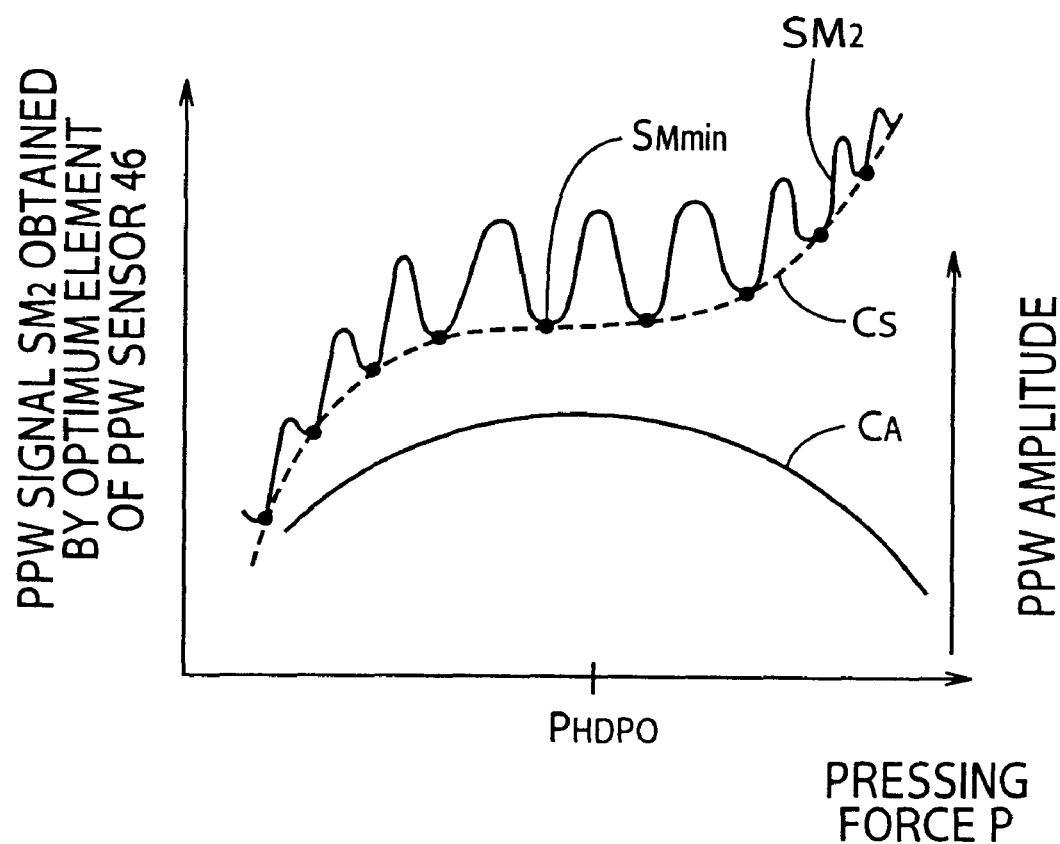
FIG. 5 is a graph for explaining the manner in which an optimum pressing force, $P_{HDPO}$, is determined by an optimum-pressing-force determining means of the apparatus of FIG. 1.

FIG. 5 shows an example of the PPW signal $SM_2$ which is produced by the optimum pressure-sensing element of the PPW sensor 46 while the pressing force P of the pressing device 54 is continuously increased. As the pressing force P increases, the magnitude of the PPW signal $SM_2$ increases while oscillating or pulsating. In the graph of FIG. 5, the signal-magnitude-change curve $C_S$, indicated at broken line, is obtained by connecting respective magnitudes of respective predetermined periodic points (e.g., respective magnitudes, $S_{Mmin}$, of respective minimum points) of successive heartbeat-synchronous pulses of the PPW signal $SM_2$. The signal-magnitude-change curve $C_S$ includes a substantially flat portion where the magnitude of the signal $SM_2$ does not substantially change as the pressing force P increases. As the pressing force P increases in a low pressing-force range in which the wall of the radial artery 56 is not flattened yet, the magnitude of the signal $SM_2$ gradually increases because of increased reaction of the wall of the artery 56. However, as the pressing force further increases, a portion of the wall of the artery 56 supported by the radius bone located under the same 56 is flattened so that the reaction of the arterial wall does not increase and the magnitude of the signal $SM_2$ is kept constant. Therefore, the curve $C_S$ exhibits a flat portion in which the magnitude of the signal $SM_2$ does not change as the pressing force P increases and the intraarterial blood pressure is directly transmitted to the PPW sensor 46 via the flattened wall of the artery 56. As the pressing force still further increases, the reaction of the wall of the artery 56 increases again whereas the artery 56 still more flattens and the pulsation of the signal $SM_2$ decreases.

FIG. 5 also s hows an example of the amplitude-change curve $C_A$ as an envelope of respective amplitudes of the successive heartbeat-synchronous pulses of the PPW signal $SM_2$ that is produced by the optimum pressure-sensing element of the PPW sensor 46 while the pressing force P of the pressing device 54 is continuously increased. That is, the curve CA represents an alternating-current component of the signal $SM_2$. As the pressing force P increases in a low pressing-force range, the curve $C_A$ increases; and as the pressing force P further increases in a high pressing-force range, the curve $C_A$ decreases because the radial artery 56 flattens and the pulsation of the signal $SM_2$ decreases.

The means 84 determines, as the optimum pressing force $P_{HDPO}$, a value which falls in a first reference range whose center is equal to the maximum value of the curve $C_A$ and/or in a second reference range whose center is equal to the center of the flat portion of the curve $C_S$.

An optimum-pressing-force maintaining means 86 controls the pressure control valve 52 and thereby maintains the air pressure of the first pressure chamber 48 at the optimum pressing force $P_{HDPO}$ determined by the means 84.

A relationship determining means 88 determines a BP-$P_M$ relationship between blood pressure BP and PPW magnitude $P_M$, as shown in FIG. 3, based on the BP values BP measured by the BP measuring means 80 and the magnitudes $P_M$ of the PPW signal $SM_2$ produced by the optimum pressure-sensing element of the PPW sensor 46 pressed with the optimum pressing force $P_{HDPO}$. The optimum pressure-sensing element is positioned right above the radial artery 56.

An estimated-BP determining means 90 successively determines an estimated BP value MBP according to the BP-$P_M$ relationship determined by the means 88, based on a magnitude of each of successive heartbeat-synchronous pulses of the PPW represented by the PPW signal $SM_2$ produced by the optimum pressure-sensing element of the PPW sensor 46 pressed with the optimum pressing force $P_{HDPO}$.

An amplitude-change-curve displaying means 92 controls the display device 32 to display, in a two-dimensional coordinate system having a first axis indicative of pressing force P and a second axis indicative of amplitude of heartbeat-synchronous pulse of PPW, the amplitude-change curve $C_A$ representing the change of the respective amplitudes of the heartbeat-synchronous pulses of the PPW signal $SM_2$ detected by the optimum pressure-sensing element, with respect to the change of the pressing force of the pressing device 54 caused by the optimum-pressing-force determining means 84. That is, the display device 32 displays the amplitude-change curve $C_A$ which is obtained when the optimum-pressing-force determining means 84 determines the optimum pressing force $P_{HDPO}$.

A signal-magnitude-change-curve displaying means 94 controls the display device 32 to display, in a two-dimensional coordinate system having a first axis indicative of pressing force P and a second axis indicative of magnitude of PPW signal $SM_2$, the signal-magnitude-change curve $C_S$ representing the change of respective magnitudes of respective predetermined periodic points of the heartbeat-synchronous pulses of the detected PPW represented by the PPW signal $SM_2$ produced by the optimum pressure-sensing element, with respect to the change of the pressing force P of the pressing device 54 caused by the optimum-pressing-force determining means 84. That is, the display device 32 displays the signal-magnitude-change curve $C_S$ which is obtained when the optimum-pressing-force determining means 84 determines the optimum pressing force $P_{HDPO}$.

An optimum-pressing-force displaying means 96 controls the display device 32 to display, in the two-dimensional coordinate system in which the amplitude-change curve $C_A$ is displayed, and/or in the two-dimensional coordinate system in which the signal-magnitude-change curve $C_S$ is displayed, a straight line 97 as a symbol representing the optimum pressing force $P_{HDPO}$ determined by the optimum-pressing-force determining means 84.

Figure 6:
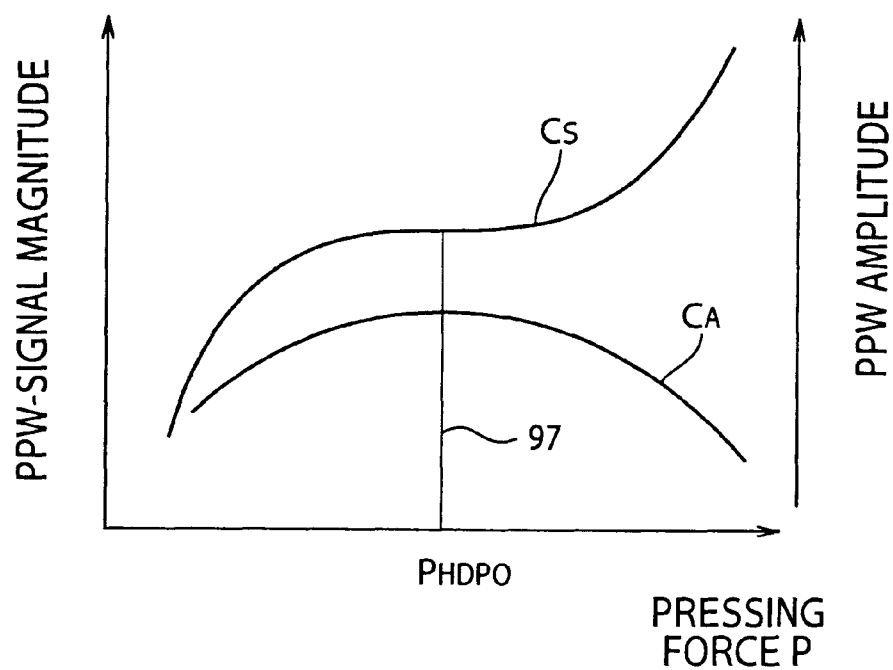
FIG. 6 is a graph which is displayed as a screen image of a display device of the apparatus of FIG. 1.

FIG. 6 shows a screen image which is displayed on the display device 32 and which includes a two-dimensional coordinate system in which the amplitude-change curve $C_A$ is displayed by the means 92, and the signal-magnitude-change curve $C_S$ is displayed by the means 94, along a common axis indicative of pressing force P of the pressing device 54. In addition, in the coordinate system, the straight line 97 representative of the optimum pressing force $P_{HDPO}$ is displayed by the means 96 such that the straight line 97 is perpendicular to the common pressing-force axis. Since the amplitude-change curve $C_A$ or the signal-magnitude-change curve $C_S$ is displayed on the display device 32, an operator who operates the present BP monitor apparatus can recognize how the PPW sensor 46 is pressed against the radial artery 56 via the body surface 38 at the time of determination of the optimum pressing force $P_{HDPO}$. FIG. 6 shows that the amplitude-change curve $C_A$ has a maximum amplitude value, substantially monotonously increases from an initial amplitude value corresponding to the initial pressing force, to the maximum amplitude value, and substantially monotonously decreases from the maximum amplitude value, and that the straight line 97 representative of the optimum pressing force $P_{HDPO}$ is displayed around the maximum amplitude value. In this case, the operator can judge that the PPW sensor 46 is appropriately pressed against the radial artery 56. In addition, FIG. 6 shows that the signal-magnitude-change curve $C_S$ includes a substantially flat portion and that the straight line 97 representative of the optimum pressing force $P_{HDPO}$ is displayed around the center of the flat portion. In this case, too, the operator can judge that the state in which the PPW sensor 46 is pressed against the radial artery 56 is appropriate.

The amplitude-change curve $C_A$ shown in FIG. 6 is a normalized curve which is obtained by normalizing the pressing-force axis with a pressing-force range (i.e., a pressing-force change width) over which the pressing force of the pressing device 54 has been changed by the optimum-pressing-force determining means 84 to determine the optimum pressing force $P_{HDPO}$, and normalizing the amplitude axis with the maximum amplitude value of the PPW signal $SM_2$ that has been obtained by the means 84 to determine the optimum pressing force $P_{HDPO}$. Similarly, the signal-magnitude-change curve $C_S$ shown in FIG. 6 is a normalized curve which is obtained by normalizing the pressing-force axis with the pressing-force range and normalizing the signal-magnitude axis with a maximum signal magnitude of the PPW signal $SM_2$ that has been obtained by the means 84 to determine the optimum pressing force $P_{HDPO}$. Therefore, even if the PPW signal $SM_2$ provides different maximum values or different amplitude values for different individual subjects, or the means 84 controls the pressing device 54 to change the pressing force P in different pressing-force ranges having different maximum pressing-force values for different individual subjects, each of the curves $C_A$, $C_S$ is always displayed in a predetermined size, so that the operator can easily recognize how the PPW sensor 46 is pressed against the radial artery 56 at the time of determination of the optimum pressing force $P_{HDPO}$.

Figure 2:
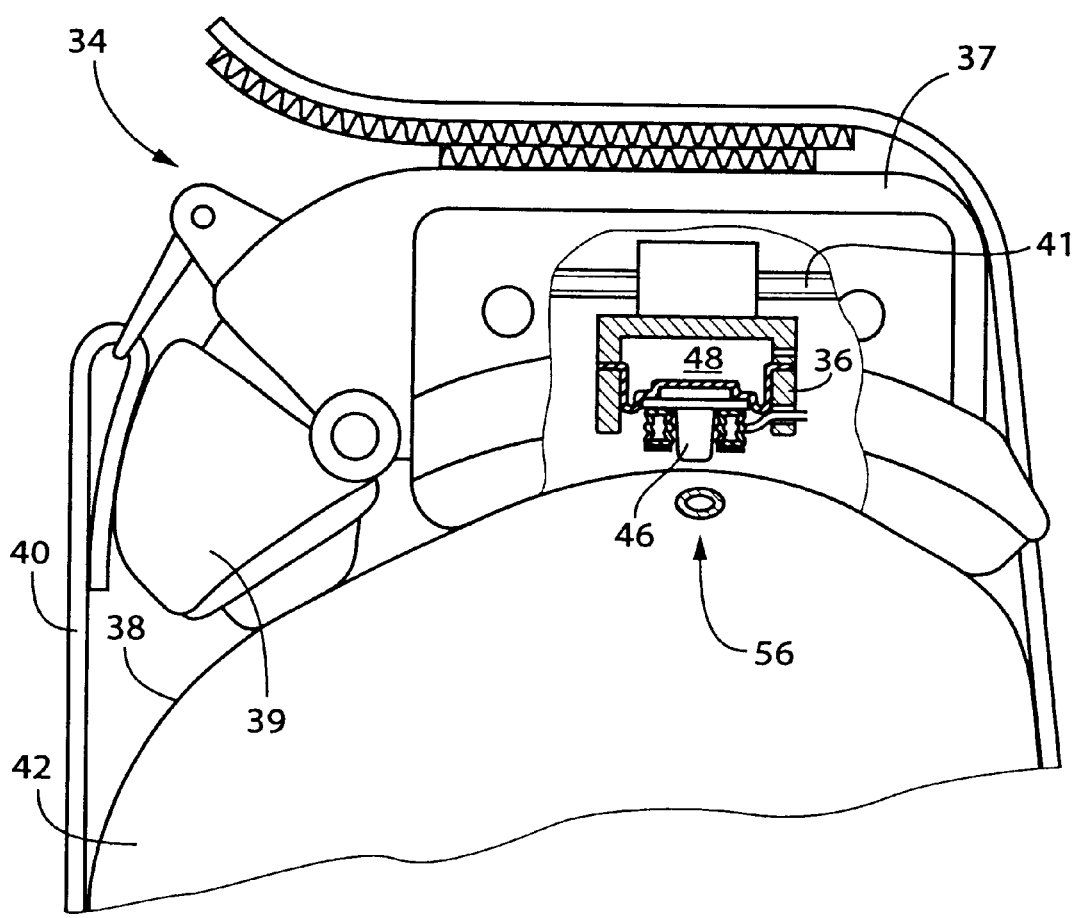
FIG. 2 is a partly cut-away, enlarged view of a pressure-pulse-wave ("PPW") detecting probe of the apparatus of FIG. 1.
Figure 7:
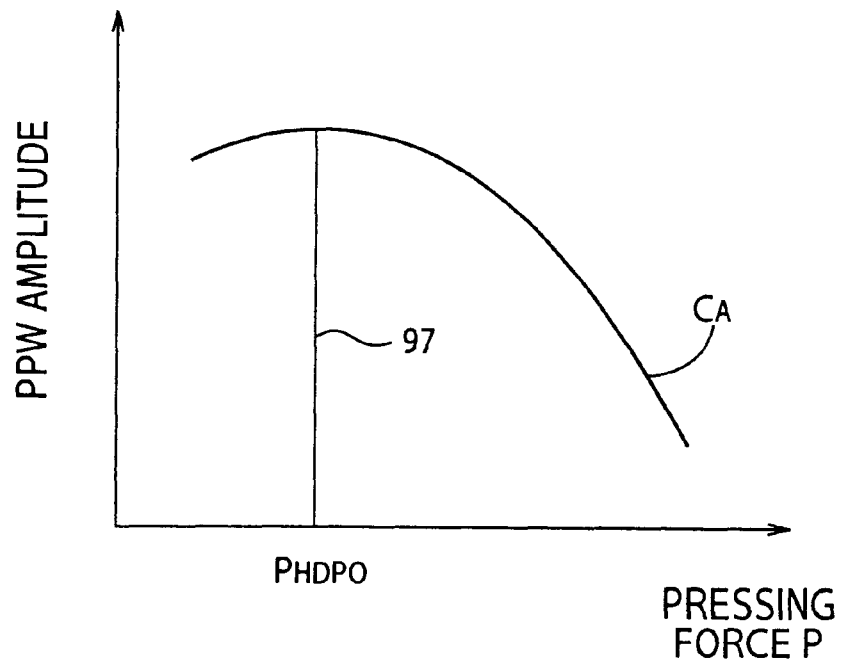
FIG. 7 is a graph which is displayed as a screen image of the display device in the case where a radial artery of a patient is shallow under body surface.

FIG. 7 shows an example of a screen image which is displayed on the display device 32 and which includes an amplitude-change curve $C_A$ only. FIG. 7 shows that the curve $C_A$ has a considerably great amplitude value at the initial or minimum pressing force of the pressing-force range, and has a maximum amplitude value at a considerably small pressing force. This amplitude-change curve $C_A$ is obtained in the case where the radial artery 56 is located at a considerably shallow position under the body surface 38 because, e.g., the patient is thin. In this case, if the press surface 62 of the protruding portion 60 of the PPW sensor 46, shown in FIGS. 1 and 2, is projecting by a considerably great amount out of the press surface 76 of the annular plate 70, an optimum pressing force $P_{HDPO}$ may be determined in a considerably unstable state in which a space may be adversely created between the body surface 38 and the press surface 76 of the annular plate 70. Therefore, the operator can judge that it will be difficult to maintain, for a long time, the appropriate state in which the PPW sensor 46 is pressed against the radial artery 56.

Figure 8:
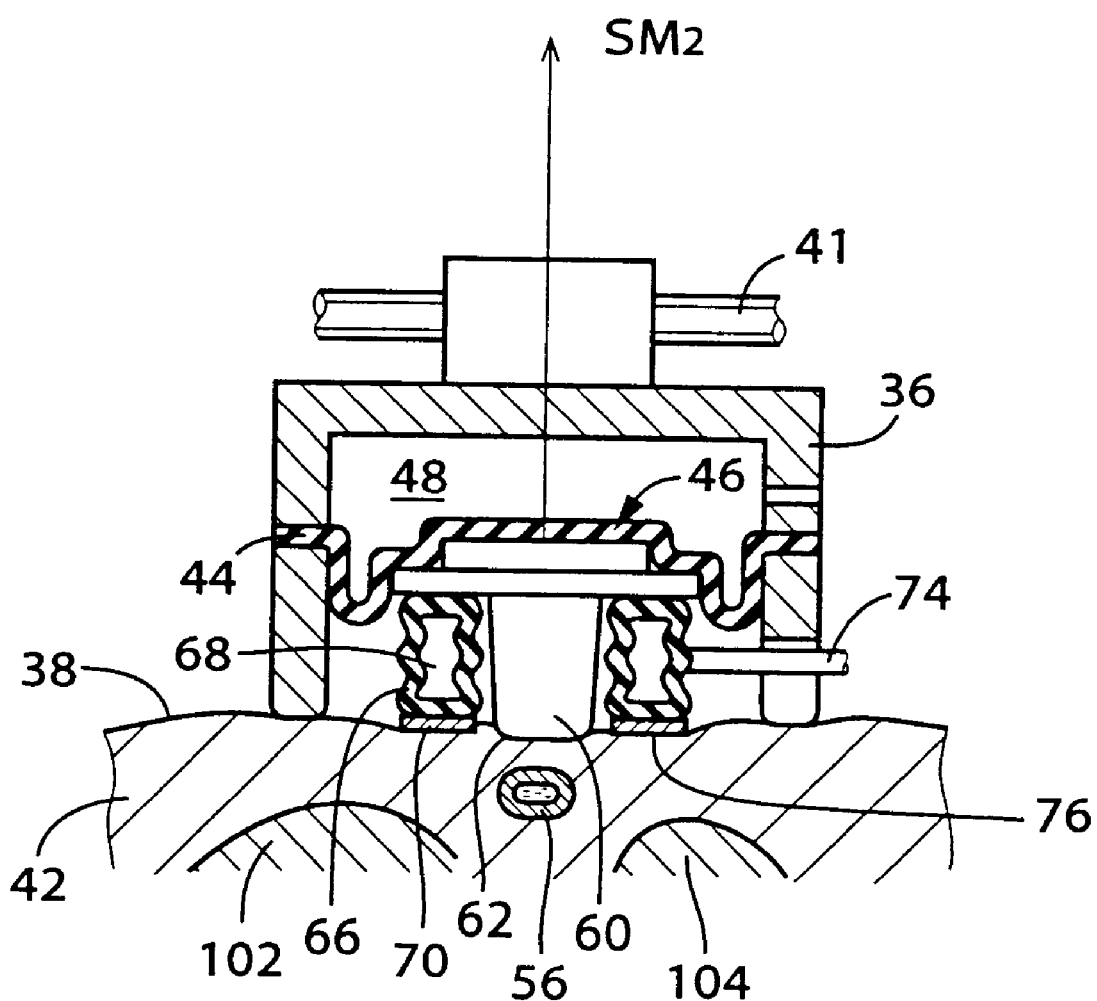
FIG. 8 is a view for explaining the manner in which a PPW sensor of the PPW detecting probe is appropriately pressed against the radial artery via the body surface in the case where the radial artery is shallow under the body surface.

When from the amplitude-change curve $C_A$ displayed on the display device 32 the operator judges, as explained above, that the state in which the PPW sensor 46 is pressed against the radial artery 56 is not appropriate, the operator can operate an operation panel (not shown) of the present BP monitor apparatus to operate the pressure control valve 72 to supply pressurized air from the air pump 50 to the second pressure chamber 68, so that the press surface 76 of the annular plate 70 is projected to a position substantially equal to the position of the press surface 62 of the protruding portion 60, as shown FIG. 8. Thus, the space present between the body surface 38 and the press surface 76 of the annular plate 70 is eliminated, and accordingly the appropriate state in which the PPW sensor 46 is pressed against the wall of the radial artery 56 can be maintained for a long time even in the case where the artery 56 is considerably shallow under the body surface 38.

Figure 9:
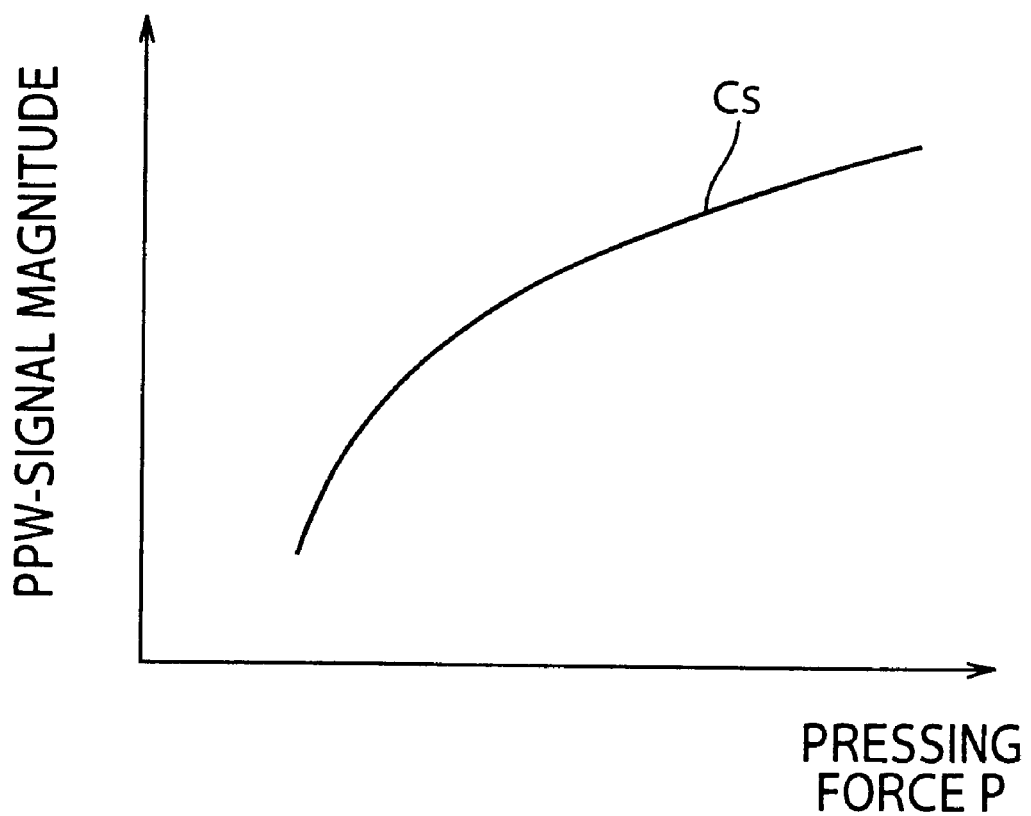
FIG. 9 is a graph which is displayed as a screen image of the display device in the case where the PPW sensor is not appropriately pressed against the radial artery.

FIG. 9 shows an example of a screen image which is displayed on the display device 32 and which includes a signal-magnitude-change curve $C_S$ only. FIG. 9 shows that as the pressing force P increases, the curve $C_S$ monotonously increases without having a flat or substantially flat portion. In this case, the operator can judge that the state in which the PPW sensor 46 is pressed against the radial artery 56 is not appropriate. This signal-magnitude-change curve $C_S$ is obtained in the case where the subject has a considerably thick skin tissue and the radial artery 56 is considerably deep under the body surface 38, but the press surface 62 of the protruding portion 60 is not projected by so great an amount out of the press surface 76 of the annular plate 70. That is, when the press surface 62 being not projected so much from the press surface 76 is used to press the radial artery 56 considerably deep under the body surface 38, the pressing device 54 must apply a great pressing force to the PPW sensor 46 to substantially flatten a portion of the wall of the artery 56. However, if the pressing device 54 cannot apply such a great pressing force, the curve $C_S$ shown in FIG. 9 is obtained.

When from the signal-magnitude-change curve $C_S$ displayed on the display device 32 the operator judges, as explained above, that the state in which the PPW sensor 46 is pressed against the artery 56 is not appropriate the operator can operate the operation panel (not shown) to operate the pressure control valve 72 to deflate the pressurized air from the second pressure chamber 68, so that the press surface 76 of the annular plate 70 is retracted from the press surface 62 of the protruding portion 60, as shown in FIG. 1. Thus, the press surface 62 of the protruding portion 60 is projected from the the press surface 76 of the annular plate 70. In this way, with a considerably small pressing force within the pressing-force range of the pressing device 54, the PPW can be appropriately pressed against the radial artery 56 which is considerably deep under the body surface 38, so that a portion of the wall of the artery 56 is substantially flattened.

A pressing-state judging means 98 judges, based on the PPW represented by the PPW signal $SM_2$ obtained while the pressing force P of the pressing device 54 is changed by the means 84, whether the state in which the PPW sensor 46 is pressed against the radial artery 56 is appropriate. More specifically described, based on the amplitude-change curve $C_A$ and the signal-magnitude-change curve $C_S$ obtained by the means 84, the judging means 98 makes a judgment. For example, the judging means 98 judges whether the amplitude-change curve $C_A$ has an amplitude value smaller than a predetermined proportion (e.g., 75%) of its maximum amplitude value, within a pressing-force range smaller than a pressing force corresponding to the maximum amplitude value. A negative judgment means that the radial artery pressed by the PPW sensor 46 is considerably shallow under the body surface 38. If the negative judgment is obtained and simultaneously the judging means 98 judges that the press surface 62 of the protruding portion 60 is projected by more than a predetermined distance from the press surface 76 of the annular plate 70, the judging means 98 judges that the state in which the PPW sensor 46 is pressed against the artery 56 is not stable.

In addition, the pressing-state judging means 98 judges, based on the signal-magnitude-change curve $C_S$, whether the curve $C_S$ has a flat or substantially flat portion, i.e., a portion in which the signal magnitude does not change as the pressing force P increases. For example, if the curve $C_S$ obtained by the means 84 is one as shown in FIG. 9, the judging means 98 makes a negative judgment. That is, if the artery 56 pressed by the PPW sensor 46 is considerably deep under the body surface 38 and simultaneously the press surface 62 of the protruding portion 60 is not projected from the press surface 76 of the annular plate 70, as shown in FIG.

8, the judging means 98 judges that the state in which the sensor 46 is pressed is not appropriate.

A projection-amount adjusting means 100 adjusts an amount of projection of the press surface 62 of them protruding portion 60 from the press surface 76 of the annular plate 70, by supplying drive signals to the air pump 50 and the pressure control valve 72 and thereby adjusting the pressure of the second pressure chamber 68, in the case where the judging means 98 judges that the state in which the PPW sensor 46 is pressed against the radial artery 56 is not appropriate, or in the case where the operator judges from the amplitude-change curve $C_A$ and/or the signal-magnitude-change curve $C_S$ displayed on the display device 32, that the state in which the sensor 46 is pressed is not appropriate, and operates the operation panel (not shown) to eliminate the inappropriate state.

Figure 10:
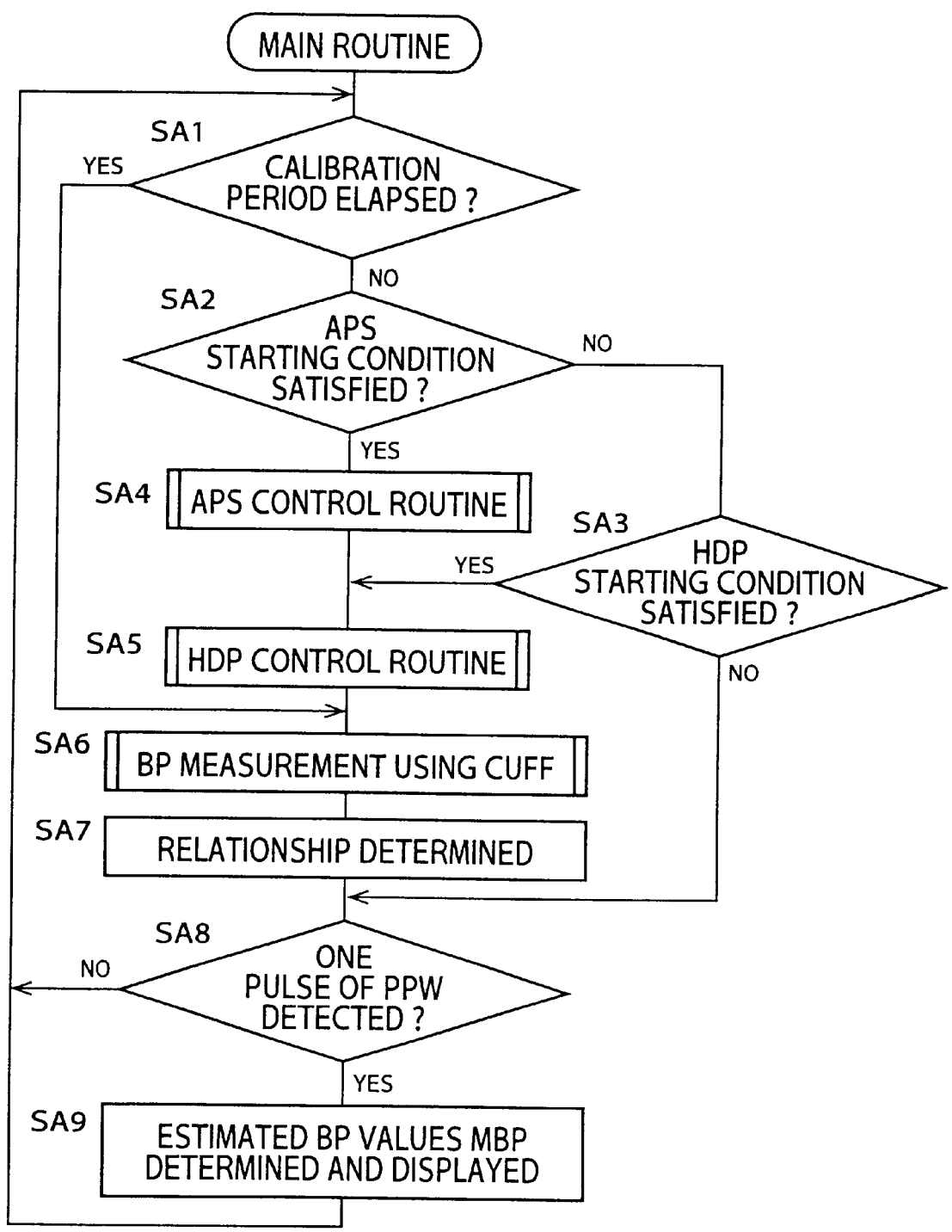
FIG. 10 is a flow chart representing a control program according to which the control device of the apparatus of FIG. 1 is operated to monitor the blood pressure BP of the patient.
Figure 11:
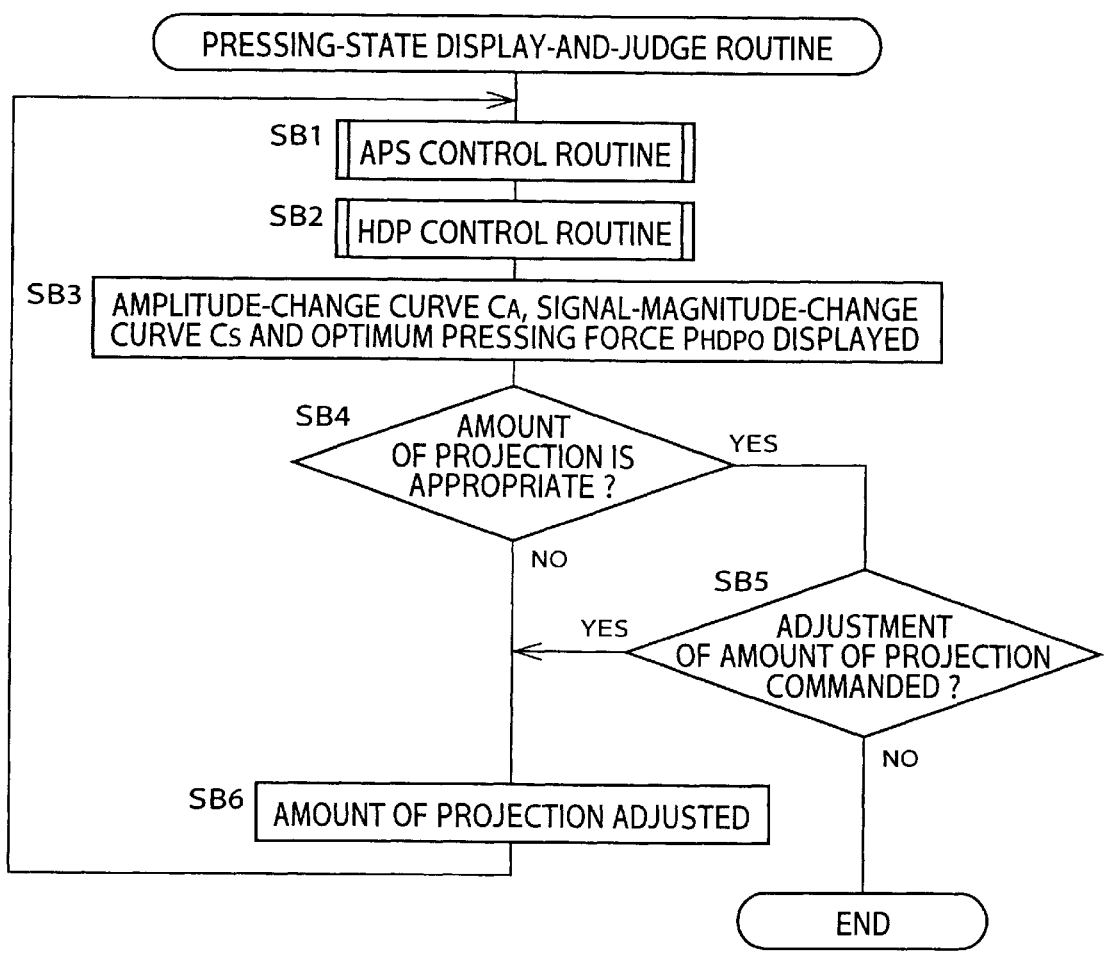
FIG. 11 is a flow chart representing a control program according to which the control device is operated, when the PPW detecting probe is initially worn on the patient, to appropriately press the PPW sensor of the probe against the radial artery of the patient.

FIGS. 10 and 11 show two flow charts representing two control programs according to which the control device 28 is operated. FIG. 10 shows a main routine, and FIG. 11 shows a pressing-state display-and-judge routine according to which the control device 28 is operated, when the PPW detecting probe 34 is initially worn on a patient, to control the display device 32 to display a state in the PPW sensor 46 is pressed against a radial artery 56 via a body surface 38, and judges whether the state in which the PPW sensor 46 is pressed is appropriate.

First, at Step SA1 of FIG. 10, the control device 28 judges whether a predetermined calibration period (e.g., from ten and several minutes to several tens of minutes) has elapsed after the BP-$P_M$ relationship had been updated at Step SA7 in the prior control cycle according to the main routine. Usually, a negative judgment is made at Step SA1, and the control of the control device 28 goes to Step SA2 to judge whether a predetermined pressing-position updating condition (hereinafter, referred to as the "APS starting condition") has been satisfied. For example, the control device 28 judges whether the active element of the PPW sensor 46 that detects the greatest amplitude of all the pressure-sensing elements of the sensor 46 is present in one of opposite end portions of the array of the pressure-sensing elements provided in the press surface 62 of the sensor 46.

If the current pressing position where the PPW sensor 46 is pressed against the radial artery 56 is within a normal range, a negative judgment is made at Step SA2, and the control goes to Step SA3 to judge whether a predetermined BP-$P_M$-relationship updating condition or a predetermined optimum-pressing-force-determination starting condition (hereinafter, referred to as the "HDP starting condition") has been satisfied. For example, the control device 28 judges whether a physical motion of the patient that changes the condition under which the PPW sensor 46 is pressed, so greatly as to change the current BP-$P_M$ relationship, or whether the monitor BP values MBP have changed by more than a predetermined amount from the standard BP value BP measured in the prior BP measurement using the cuff 10.

If a negative judgment is made at Step SA3, the control of the control device 28 goes to Step SA8 to judge, based on the PPW signal $SM_2$ supplied from the optimum (active) element of the PPW sensor 46 pressed with the optimum pressing force $P_{HDPO}$, whether one heartbeat-synchronous pulse of the PPW has been detected by the PPW sensor 46. If a negative judgment is made at Step SA8, Steps SA1, SA2, SA3, and SA8 are repeated. Meanwhile, if a positive judgment is made, the control goes to Step SA9 corresponding to the estimated-BP determining means 90. At Step SA9, the control device 28 determines, based on the detected one pulse of the PPW, a maximum magnitude $P_{Mmax}$ and a minimum magnitude $P_{Mmin}$ of the one pulse, determines an estimated systolic BP value $MBP_{SYS}$ and an estimated diastolic BP value $MBP_{DIA}$ according to the current BP-$P_M$ relationship based on the determined maximum magnitude $P_{Mmax}$ and minimum magnitude $P_{Mmin}$ of the one pulse, respectively, and controls the display device 32 to display, in digits, the estimated or monitor systolic and diastolic BP values $MBP_{SYS}$, $MBP_{DIA}$ determined for the one pulse. In addition, the control device 32 calibrates the continuous waveform of the one pulse of the PPW represented by the PPW signal $SM_2$, according to the current BP-$P_M$ relationship, and controls the display device 32 to display the thus calibrated continuous waveform representing the estimated BP values of the patient.

If a positive judgment is made at Step SA1 while Steps SA1 to SA3, SA8, and SA9 are repeated, the control of the control device 28 goes to Step SA6 to carry out a BP measurement using the cuff 10, and then to Step SA7 to update the current BP-$P_M$ relationship, and then to Steps SA8, SA9. More specifically described, at Step SA6 corresponding to the BP measuring means 80, the control device 28 switches the deflation control valve 16 to its pressure-supply state and actuates the air pump 18 to increase the pressure of the cuff 10 up to a predetermined target value (e.g., 180 mmHg) higher than an estimated systolic BP value of the patient, and subsequently stops the pump 18 and switches the control valve 16 to its slow-deflation state to decrease the pressure of the cuff 10 at a predetermined low rate of, e.g., 3 mmHg/sec. Based on change of respective amplitudes of successive heartbeat-synchronous pulses of the pulse wave represented by the pulse-wave signal $SM_1$ obtained during the slow deflation of the cuff 10, the control device 28 determines a systolic, a mean, and a diastolic BP values $BP_{SYS}$, $BP_{MEAN}$, $BP_{DIA}$ (i.e., standard BP values), according to a well-known oscillometric BP-determine algorithm. In addition, based on an interval between two successive heartbeat-synchronous pulses of the pulse wave, the control device 28 determines a pulse rate (i.e., heart rate) of the patient. The control device 28 controls the display device 32 to display, in digits, the thus measurerd BP values and pulse rate, and switches the deflation control valve 16 to its quick-deflation state to quickly deflate the cuff 10.

Step SA6 is followed by Step SA7 corresponding to the relationship determining means 88. At Step SA7, the control device 28 determines a new BP-$P_M$ relationship based on magnitudes of the PPW detected by the optimum element of the PPW sensor (i.e., magnitudes of the PPW signal $SM_2$) and the BP values $BP_{SYS}$, $BP_{DIA}$ measured using the cuff 10 at Step SA6, and updates the current BP-$P_M$ relationship with the thus determined new BP-$P_M$ relationship. More specifically described, the control device 28 reads in one heartbeat-synchronous pulse of the PPW detected by the optimum element of the PPW sensor 46, determines, based on the read-in one pulse of the PPW, a maximum magnitude $P_{Mmax}$ and a minimum magnitude $P_{Mmin}$ Of the one pulse, and determines a new relationship between blood pressure BP and PPW magnitude, as shown in FIG. 3, based on the thus determined maximum and minimum magnitudes $P_{Mmax}$, $P_{Mmin}$ of the one pulse, and the systolic and diastolic BP values $BP_{SYS}$, $BP_{DIA}$ measured using the cuff 10 at Step SA6.

If the APS starting condition is satisfied, for example, if the pressing position where the PPW sensor 46 is pressed against the radial artery 56 is moved out of position, a positive judgment is made at Step SA2, and the control goes to Step SA4, i.e., an APS control routine corresponding to the optimum-pressing-position determining means 82.

According to the APS control routine, the control device 28 controls the pressing device 54 to press the PPW sensor 46 with a predetermined pressing force which is sufficiently smaller than the optimum pressing force $P_{HDPO}$, determines, based on the respective PPW signals $SM_2$ supplied from the pressure-sensing elements of the PPW sensor 46, an active element that detects the greatest amplitude of all the elements of the PPW sensor 46, and determines an optimum pressing position where the active element of the PPW sensor 46 is determined as one located around the center of the array of elements of the sensor 46. After the PPW sensor 46 is thus positioned at the optimum pressing position and the active element of the sensor 46 is selected as an optimum element of the same 46, the control goes to Step SA5, i.e., a HDP control routine. According to the HDP control routine, the control device 28 controls the pressing device 54 to continuously increase the pressing force P applied to the PPW sensor 46, determines, as a new optimum pressing force $P_{HDpO}$, a pressing force of the pressing device 54 at which respective amplitudes of successive heartbeat-synchronous pulses of the PPW detected by the optimum element of the PPW sensor 46, positioned right above the radial artery 56, take a maximum value during the increasing of the pressing force P, and updates the current optimum pressing force $P_{HDPO}$ with the thus determined new optimum pressing force $P_{HDPO}$. The control device 28 maintains the pressing force P of the pressing device 54 at the updated optimum pressing force $P_{HDPO}$. Thus, Step SA5 corresponds to the optimum-pressing-force determining means 84 and the optimum-pressing-force maintaining means 86. Then, in the state in which the PPW sensor 46 is pressed with the optimum pressing force $P_{HDpO}$, the control device 28 carries out Step SA6 and the following steps.

If a negative judgment is made at Step SA2, that is, if it is judged that the PPW sensor 46 is pressed at an appropriate position and the BP of the patient can be continuously monitored by the present apparatus, but if a positive judgment is made at Step SA3, the control device 28 carries out the HDP control routine of Step SA5, and then the following steps.

Next, by reference to FIG. 11, there will be described the pressing-state display-and-judge routine according to which the control device 28 is operated, when the PPW detecting probe 34 is initially worn on the patient, and before the control device 28 is operated according to the main routine of FIG. 10. According to the display-and-judge routine, the control device 28 controls the display device 32 to display a state in the PPW sensor 46 is pressed against the radial artery 56 via the body surface 38, and judges whether the state in which the PPW sensor 46 is pressed is appropriate.

First, at Step SB1 of FIG. 11, corresponding to the optimum-pressing-position determining means 82, the control device 28 carries out the same APS control routine as that employed at Step SA4 of FIG. 10. In short, the control device 28 determines, based on the respective PPW signals $SM_2$ supplied from the pressure-sensing elements of the PPW sensor 46, an optimum pressing position where the active element of the sensor 46 that detects the greatest amplitude of all the elements of the sensor 46 is one located in the vicinity of the center of the array of elements provided in the press surface 62 of the sensor 46.

Step SB1 is followed by Step SB2 corresponding to the optimum-pressing-force determining means 84. At this step, the control device 28 controls the pressing device 54 to continuously increase the pressing force P applied to the PPW sensor 46, and obtains an amplitude-change curve $C_A$ and a signal-magnitude-change curve $C_S$ from the PPW signal $SM_2$ supplied from the optimum element of the PPW sensor 46 during the continuous increasing of the pressing force. In addition, the control device 28 determines, as an optimum pressing force $P_{HDPO}$, a pressing force corresponding to the center of an overlapping portion of (a) a first predetermined pressing-force range whose center corresponds to the maximum amplitude value of the amplitude-change curve $C_A$ and (b) a second predetermined pressing-force range whose center corresponds to the center of the flat portion of the signal-magnitude-change curve $C_S$.

Step SB2 is followed by Step SB3 to normalize the amplitude-change curve $C_A$ and the signal-magnitude-change curve $C_S$ obtained when the optimum pressing force $P_{HDPO}$ is determined at Step SB2, and control the display device 32 to display the normalized curves $C_A$, $C_S$ in the two-dimensional coordinate system having the common pressing-force axis and the PPW-amplitude axis or the PPW-signal-magnitude axis, and additionally display the straight line 97 indicative of the optimum pressing force $P_{HDPO}$ on the common pressing-force axis. Thus, Step SB3 corresponds to the amplitude-change-curve displaying means 92, the signal-magnitude-change-curve displaying means 94, and the optimum-pressing-force displaying means 96. FIG. 6 shows an example of the screen image displayed on the display device 32 at Step SB3 when the state in which the PPW sensor 46 is pressed against the radial artery 56 is appropriate.

Step SB3 is followed by Step SB4 corresponding to the pressing-state judging means 98. At Step SB4, the control device 28 judges, in the state in which the press surface 62 of the protruding portion 60 is projected from the press surface 76 of the annular plate 70 by more than a predetermined amount, as shown in FIG. 1, whether the amplitude-change curve $C_A$ obtained at Step SB2 has an amplitude value smaller than 75% of its maximum amplitude value, in a pressing-force range whose upper limit is equal to a pressing force corresponding to the maximum amplitude value, or whether the signal-magnitude-change curve $C_S$ obtained at Step SB2 has a flat or substantially flat portion. If at least one of those two judgments is negative, the control device 28 judges that the state in which the PPW sensor 46 is pressed against the radial artery 56 is not appropriate.

If a negative judgment is made at Step SB4, the control goes to Step SB6 corresponding to the projection-amount adjusting means 100. At this step, the control device 28 supplies drive signals to the air pump 50 and the pressure control valve 72 to adjust the pressure in the second pressure chamber 68 and thereby adjust the amount of projection of the press surface 62 of the protruding portion 60 from the press surface 76 of the annular plate 70, so that the PPW sensor 46 is appropriately pressed against the radial artery 56. Then, the control device 28 repeats Step SB1 and the following steps.

On the other hand, if a positive judgment is made at Step SB4, the control goes to Step SB5 to judge whether the operator who has judged that the state in which the sensor 46 is pressed is not appropriate has operated the operation panel (not shown) to adjust the amount of projection of the press surface 62 of the protruding portion 60 from the press surface 76 of the annular plate 70. Even though a negative judgment may not be made at Step SB4, the operator may judge, based on the curves $C_A$, $C_S$ displayed on the display device 32 at Step SB3, that the state in which the sensor 46 is pressed is not appropriate. In this case, the operator can adjust the amount of projection of the press surface 62 of the protruding portion 60 from the press surface 76 of the annular plate 70, by operating the operation panel.

If a positive judgment is made at Step SB5, the control proceeds with Step SB6 to adjust the amount of projection of the press surface 62 according to the operation of the operation panel, and then goes back to Step SB1. However, if a negative judgment is made at Step SB5, the control device 28 quits the display-and-judge routine of FIG. 11 and enters the main routine of FIG. 10.

It emerges from the foregoing description that in the illustrated embodiment the amplitude-change-curve displaying means 92 (Step SB3) displays the amplitude-change curve $C_A$ which represents the change of the respective amplitudes of the successive heartbeat-synchronous pulses of the PPW detected by the optimum element of the PPW sensor 46, with respect to the change of the pressing force P of the pressing device 54 caused by the optimum-pressing-force determining means 84 (Step SB2). Therefore, the operator who operates the present BP monitor apparatus can recognize how the PPW sensor 46 is pressed against the radial artery 56 at the time of determination of the optimum pressing force $P_{HDPO}$.

In the illustrated embodiment, the signal-magnitude-change-curve displaying means 94 (Step SB3) displays, on the display device 32, the signal-magnitude-change curve $C_S$ which represents the change of the respective magnitudes of the respective periodic minimum points of successive heartbeat-synchronous pulses of the PPW detected by the optimum element of the PPW sensor 46, with respect to the change of the pressing force P of the pressing device 54 caused by the optimum-pressing-force determining means 84 (Step SB2). Therefore, the operator-who operates the present BP monitor apparatus can judge whether the state in which the PPW sensor 46 is pressed against the radial artery 56 at the time of determination of the optimum pressing force $P_{HDpO}$ is appropriate.

In the illustrated embodiment, the optimum-pressing-force displaying means 96 (Step SB3) displays, in the two-dimensional coordinate system in which the amplitude-change curve $C_A$ or the signal-magnitude-change curve $C_S$, the straight line 97 indicative of the optimum pressing force $P_{HDPO}$. Thus, the operator can judge whether the optimum pressing force $P_{HDPO}$ has been determined at an appropriate pressing force.

In the illustrated embodiment, the pressing-state judging means 98 (Step SB4) can identify the inappropriate state in which a space is left between the annular plate 70 of the PPW sensor 46 and the body surface 38 because the radial artery 56 is too shallow under the body surface 38 and accordingly the optimum pressing force $P_{HDPO}$ determined by the means 84 (Step SB2) is too small, and the inappropriate state in which the PPW sensor 46 cannot be pressed with a sufficiently great pressing force because the radial artery 56 is too deep under the body surface 38 and accordingly the optimum pressing force $P_{HDPO}$ determined by the means 84 (Step SB2) is too great to be applied by the pressing device 54. Thus, the control device 28 can automatically judge whether the state in which the PPW sensor 46 is pressed against the radial artery 56 is appropriate.

While the present invention has been described in its preferred embodiments, the present invention may be otherwise embodied.

For example, in the illustrated embodiment, the pressing-state judging means 98 (Step SB4) automatically judges whether the state in which the PPW sensor 46 is pressed against the radial artery 56 is appropriate. However, it is possible to omit the judging means 98.

In the illustrated embodiment, the PPW sensor 46 is appropriately pressed against the radial artery 56, by the adjustment of the amount of projection of the press surface 62 of the protruding portion 60 from the press surface 76 of the annular plate 70, irrespective of whether the artery 56 may be considerably shallow or considerably deep under the body surface 38. However, it is possible to employ and use a PPW detecting probe 34 which has a single sort of PPW sensor 46 which has an amount of projection of its press surface 62 that just corresponds to the depth of the radial artery 56 under the body surface 38, or to select and use one of a plurality of sorts of PPW sensors 46 that has an amount of projection of its press surface 62 that just corresponds to the depth of the radial artery 56 under the body surface 38 and detachably attach the selected PPW sensor 46 to a PPW detecting probe 34.

In the illustrated embodiment, the optimum-pressing-force displaying means 96 displays the straight line 97 indicative of the optimum pressing force $P_{HDpO}$. However, it is possible to use any other symbol than the straight line 97 so long as the symbol can indicate the optimum pressing force $P_{HDPO}$ and can be displayed with the amplitude-change curve $C_A$ or the signal-magnitude-change curve $C_S$.

In the illustrated embodiment, the PPW is detected from the radial artery 56. However, a PPW may be detected from any other artery than the radial artery 56, such as a dorsal pedal artery.

It is to be understood that the present invention may be embodied with other changes, improvements, and modifications that may occur to one skilled in the art without departing from the scope and spirit of the invention defined in the appended claims.

What is claimed is:

1. A blood-pressure monitor apparatus for monitoring a blood pressure of a living subject, comprising:

a pressure-pulse-wave sensor which includes a plurality of pressure sensing elements which are arranged in a reference direction and each of which detects a pressure pulse wave propagated thereto from an arterial vessel of the subject and produces a pressure-pulse-wave signal representing the detected pressure pulse wave that includes a plurality of heartbeat-synchronous pulses, the pressure-pulse-wave sensor having a press surface which supports the pressure sensing elements arranged in the reference direction and which is adapted to be pressed against the arterial vessel via a body surface of the subject such that the arranged pressure sensing elements intersect the arterial vessel;

a pressing device which presses, with a pressing force, the pressure-pulse-wave sensor against the arterial vessel via the body surface;

optimum-element selecting means for selecting, as an optimum element, one of the pressure sensing elements that provides the detected pressure pulse wave including a heartbeat-synchronous pulse whose amplitude is greatest of respective amplitudes of respective heartbeat-synchronous pulses of the detected pressure pulse waves provided by, the pressure sensing elements;

optimum-pressing-force determining means for changing the pressing force of the pressing device and determining, based on the pressure pulse wave detected by the optimum element while the pressing force is changed, an optimum pressing force with which the pressing device presses the pressure-pulse wave sensor against the arterial vessel via the body surface such that a portion of a wall of the arterial vessel is substantially flattened;

optimum-pressing-force maintaining means for maintaining the optimum pressing force of the pressing device;

estimated-blood-pressure determining means for determining an estimated blood pressure according to a predetermined relationship between blood pressure and magnitude of pressure pulse wave, based on a magnitude of each of a plurality of heartbeat-synchronous pulses of the detected pressure pulse wave represented by the pressure-pulse-wave signal produced by the optimum element in a state in which the pressure-pulse-wave sensor is pressed against the arterial vessel with the optimum pressing force maintained by the optimum-pressing-force maintaining means; and an amplitude-change-curve displaying device which displays, in a two-dimensional coordinate system having a first axis indicative of pressing force and a second axis indicative of amplitude of heartbeat-synchronous pulse of pressure pulse wave, an amplitude-change curve representing a change of the respective amplitudes of the heartbeat-synchronous pulses of the pressure pulse wave detected by the optimum element, with respect to a change of the pressing force of the pressing device caused by the optimum-pressing-force determining means.

2. An apparatus according to claim 1, further comprising an estimated-blood-pressure displaying device which displays the estimated blood pressure determined by the estimated-blood-pressure determining means.

3. An apparatus according to claim 1, further comprising an optimum-pressing-force displaying device which displays, in the two-dimensional coordinate system in which the amplitude-change curve is displayed, a symbol representing the optimum pressing force determined by the optimum-pressing-force determining means.

4. An apparatus according to claim 1, further comprising judging means for judging, based on the pressure pulse wave detected by the optimum element while the pressing force is changed by the optimum-pressing-force determining means, whether the pressing device appropriately presses the pressure-pulse-wave sensor against the arterial vessel via the body surface.

5. An apparatus according to claim 1, further comprising:
a blood-pressure measuring device which includes an inflatable cuff adapted to be wound around a body portion of the subject and measures at least one blood pressure value of the subject based on a pulse wave transmitted to the cuff while an air pressure in the cuff is changed; and
a relationship determining means for determining the relationship between blood pressure and magnitude of pressure pulse wave, based on said at least one blood pressure value measured by the blood-pressure measuring device and at least one magnitude of a heartbeat-synchronous pulse of the pressure pulse wave detected by the optimum element in the state in which the pressure-pulse-wave sensor is pressed against the arterial vessel with the optimum pressing force maintained by the optimum-pressing-force maintaining means.

6. A blood-pressure monitor apparatus for monitoring a blood pressure of a living subject, comprising:
a pressure-pulse-wave sensor which includes a plurality of pressure sensing elements which are arranged in a reference direction and each of which detects a pressure pulse wave propagated thereto from an arterial vessel of the subject and produces a pressure-pulse-wave signal representing the detected pressure pulse wave that includes a plurality of heartbeat-synchronous pulses, the pressure-pulse-wave sensor having a press surface which supports the pressure sensing elements arranged in the reference direction and which is adapted to be pressed against the arterial vessel via a body surface of the subject such that the arranged pressure sensing elements intersect the arterial vessel;

a pressing device which presses, with a pressing force, the pressure-pulse-wave sensor against the arterial vessel via the body surface;

optimum-element selecting means for selecting, as an optimum element, one of the pressure sensing elements that provides the detected pressure pulse wave including a heartbeat-synchronous pulse whose amplitude is greatest of respective amplitudes of respective heartbeat-synchronous pulses of the detected pressure pulse waves provided by the pressure sensing elements;

optimum-pressing-force determining means for changing the pressing force of the pressing device and determining, based on the pressure pulse wave detected by the optimum element while the pressing force is changed, an optimum pressing force with which the pressing device presses the pressure-pulse wave sensor against the arterial vessel via the body surface such that a portion of a wall of the arterial vessel is substantially flattened;

optimum-pressing-force maintaining means for maintaining the optimum pressing force of the pressing device;

estimated-blood-pressure determining means for determining an estimated blood pressure according to a predetermined relationship between blood pressure and magnitude of pressure pulse wave, based on a magnitude of each of a plurality of heartbeat-synchronous pulses of the detected pressure pulse wave represented by the pressure-pulse-wave signal produced by the optimum element in a state in which the pressure-pulse-wave sensor is pressed against the arterial vessel with the optimum pressing force maintained by the optimum-pressing-force maintaining means; and a signal-magnitude-change-curve displaying device which displays, in a two-dimensional coordinate system having a first axis indicative of pressing force and a second axis indicative of magnitude of pressure-pulse-wave signal, a signal-magnitude-change curve representing a change of respective magnitudes of respective predetermined periodic points of the heartbeat-synchronous pulses of the detected pressure pulse wave represented by the pressure-pulse-wave signal produced by the optimum element, with respect to a change of the pressing force of the pressing device caused by the optimum-pressing-force determining means.

7. An apparatus according to claim 6, further comprising an estimated-blood-pressure displaying device which displays the estimated blood pressure determined by the estimated-blood-pressure determining means.

8. An apparatus according to claim 6, further comprising an optimum-pressing-force displaying device which displays, in the two-dimensional coordinate system in which the signal-magnitude-change curve is displayed, a symbol representing the optimum pressing force determined by the optimum-pressing-force determining means.

9. An apparatus according to claim 6, further comprising judging means for judging, based on the pressure pulse wave detected by the optimum element while the pressing force is changed by the optimum-pressing-force determining means, whether the pressing device appropriately presses the pressure-pulse-wave sensor against the arterial vessel via the body surface.

10. An apparatus according to claim 6, further comprising:
- a blood-pressure measuring device which includes an inflatable cuff adapted to be wound around a body portion of the subject and measures at least one blood pressure value of the subject based on a pulse wave transmitted to the cuff while an air pressure in the cuff is changed; and
- a relationship determining means for determining the relationship between blood pressure and magnitude of pressure pulse wave, based on said at least one blood pressure value measured by the blood-pressure measuring device and at least one magnitude of a heartbeat-synchronous pulse of the pressure pulse wave detected by the optimum element in the state in which the pressure-pulse-wave sensor is pressed against the arterial vessel with the optimum pressing force maintained by the optimum-pressing-force maintaining means.

* * * * *